(12) United States Patent
Bauer et al.

(10) Patent No.: US 11,918,472 B2
(45) Date of Patent: *Mar. 5, 2024

(54) HOLLOW SLEEVE AUGMENT DEVICE AND TOOL

(71) Applicant: WALDEMAR LINK GmbH & Co. KG, Hamburg (DE)

(72) Inventors: Eckhard Bauer, Kiel (DE); Helmut D. Link, Hamburg (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 56 days.

This patent is subject to a terminal disclaimer.

(21) Appl. No.: 17/809,904

(22) Filed: Jun. 30, 2022

(65) Prior Publication Data

US 2022/0331113 A1 Oct. 20, 2022

Related U.S. Application Data

(63) Continuation of application No. 15/742,697, filed as application No. PCT/EP2016/064728 on Jun. 24, 2016, now Pat. No. 11,406,501.

(30) Foreign Application Priority Data

Jul. 9, 2015 (EP) .................................... 15176128

(51) Int. Cl.
*A61F 2/30* (2006.01)
*A61F 2/46* (2006.01)

(52) U.S. Cl.
CPC ............ *A61F 2/30734* (2013.01); *A61F 2/46* (2013.01); *A61F 2002/30471* (2013.01);
(Continued)

(58) Field of Classification Search
CPC ............... A61F 2002/30738; A61F 2002/4615
See application file for complete search history.

(56) References Cited

U.S. PATENT DOCUMENTS 4,065,817 A 1/1978 Branemark et al.
4,519,101 A 5/1985 Schreiber et al.
(Continued)

FOREIGN PATENT DOCUMENTS

AU 2009202171 A1 12/2009
CN 1120926 A 4/1996
(Continued)

OTHER PUBLICATIONS

Communication Pursuant to Article 94(3) EPC dated Jun. 3, 2022, in connection with European Patent Application No. 16731922.7, 7 pgs.
(Continued)

*Primary Examiner* — Megan Y Wolf
(74) *Attorney, Agent, or Firm* — Chiesa Shahinian & Giantomasi PC

(57) ABSTRACT

An augment device includes a hollow sleeve surrounding a channel extending through the hollow sleeve from a top to a bottom of the hollow sleeve, the hollow sleeve comprising a wall having an inner face and an outer face. The hollow sleeve includes at least one bending joint, the bending joint being configured for compressing the channel. Thereby the hollow sleeve may be compressed under an external force, leading to a decreased circumference and width of the hollow sleeve. This leads to a gap between the perimeter of the augment device and surrounding bone material, breaking any connections, By virtue of this, a much facilitated removal of the augment device can be achieved. Further, an extraction tool includes grippers for engaging and compress-
(Continued)

ing the augment device, and further instruments, particularly a jig, for achieving an effective removal.

19 Claims, 6 Drawing Sheets

(52) U.S. Cl.
CPC ............... *A61F 2002/30545* (2013.01); *A61F 2002/30617* (2013.01); *A61F 2002/30736* (2013.01); *A61F 2002/30738* (2013.01); *A61F 2002/4615* (2013.01); *A61F 2002/4619* (2013.01); *A61F 2002/4628* (2013.01)

(56) References Cited

U.S. PATENT DOCUMENTS

| | | |
|---|---|---|
| 4,846,839 A | 7/1989 | Noiles |
| 4,961,748 A | 10/1990 | Frey et al. |
| 5,108,432 A | 4/1992 | Gustavson |
| 5,250,049 A | 10/1993 | Michael |
| 5,571,204 A | 11/1996 | Nies |
| 5,766,262 A | 6/1998 | Mikhail |
| 8,506,645 B2 | 8/2013 | Blaylock et al. |
| 11,357,631 B2 | 6/2022 | Bauer et al. |
| 11,406,501 B2 | 8/2022 | Bauer et al. |
| 11,751,996 B2 * | 9/2023 | Bauer .................... A61F 2/389 623/20.16 |
| 2003/0033019 A1 | 2/2003 | Lob |
| 2003/0065397 A1 | 4/2003 | Hanssen et al. |
| 2004/0010315 A1 | 1/2004 | Song |
| 2004/0019386 A1 | 1/2004 | Ferree |
| 2004/0024469 A1 | 2/2004 | Ferree |
| 2004/0162619 A1 | 8/2004 | Blaylock et al. |
| 2005/0107883 A1 | 5/2005 | Goodfried et al. |
| 2006/0142858 A1 | 6/2006 | Colleran et al. |
| 2007/0073387 A1 | 3/2007 | Forster et al. |
| 2008/0262626 A1 | 10/2008 | Raugel |
| 2009/0171389 A1 | 7/2009 | Sankaran |
| 2010/0057212 A1 | 3/2010 | Thomas |
| 2010/0114323 A1 | 5/2010 | Deruntz et al. |
| 2011/0009974 A1 | 1/2011 | Blaylock et al. |
| 2011/0066192 A1 | 3/2011 | Frasier et al. |
| 2011/0202141 A1 | 8/2011 | Metzger et al. |
| 2012/0016482 A1 | 1/2012 | Mooradian et al. |
| 2012/0016485 A1 | 1/2012 | Sharp |
| 2012/0089227 A1 | 4/2012 | Jarzem |
| 2013/0150858 A1 | 6/2013 | Primiano et al. |
| 2013/0172892 A1 | 7/2013 | Servidio et al. |
| 2014/0081410 A1 | 3/2014 | Lieberman et al. |
| 2014/0099353 A1 | 4/2014 | Link |
| 2014/0207123 A1 | 7/2014 | Mueller |
| 2014/0277528 A1 | 9/2014 | Mines et al. |
| 2014/0277551 A1 | 9/2014 | Lindsay et al. |

FOREIGN PATENT DOCUMENTS

| | | |
|---|---|---|
| CN | 101172061 A | 5/2008 |
| CN | 103764180 A | 4/2014 |
| CN | 104042362 A | 9/2014 |
| CN | 204111781 U | 1/2015 |
| EP | 0281984 A1 | 9/1988 |
| EP | 2130516 A1 | 12/2009 |
| EP | 2756825 A1 | 7/2014 |
| FR | 2646768 A | 11/1990 |
| JP | 2009-291608 A | 12/2009 |
| WO | 2013/102089 A1 | 7/2013 |
| WO | 2015/145348 A1 | 10/2015 |

OTHER PUBLICATIONS

Office Action dated Apr. 7, 2020, in connection with Japanese Patent Application No. 2018-500480 and its English translation.
International Search Report and Written Opinion dated Sep. 1, 2016, in connection with International Patent Application No. PCT/EP2016/064728, 11 pgs.
Office Action dated Apr. 30, 2021 in connection with Canadian Patent Application No. 2,991,536.
Translation of EP0281984 retrieved from espacenet on May 8, 2020 (Year: 2020).
Office Action dated Jan. 24, 2019, in connection with Chinese Patent Application No. 201680040563.0.
International Search Report and Written Opinion dated Feb. 17, 2017, directed to PCT/EP2016/064728, 16 pgs.
Non-Final Office Action dated Mar. 2, 2023, in connection with U.S. Appl. No. 17/663,414, filed May 13, 2022, 20 pgs.

* cited by examiner

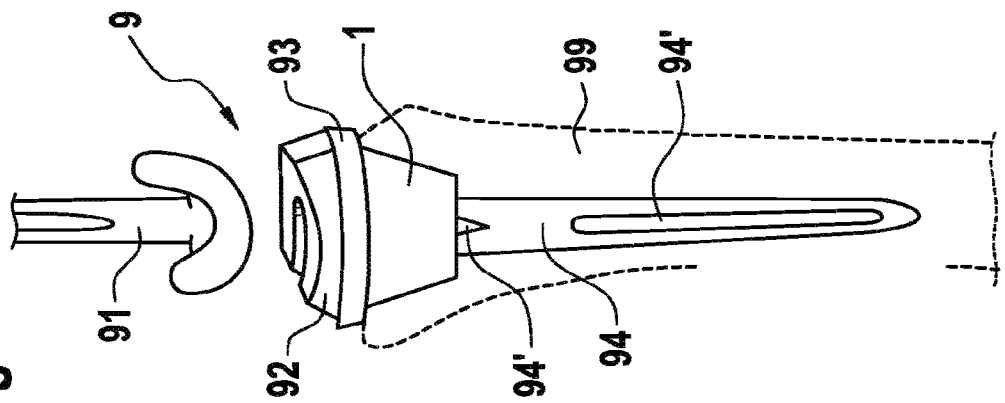
Fig. 2
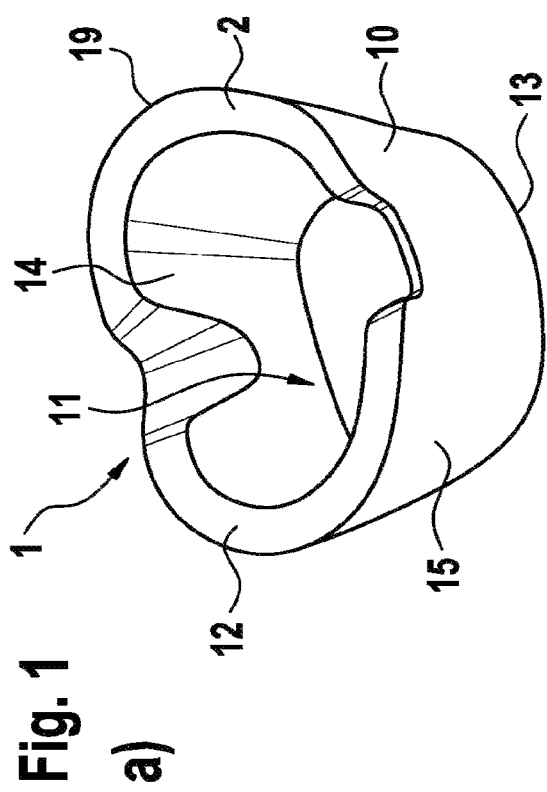
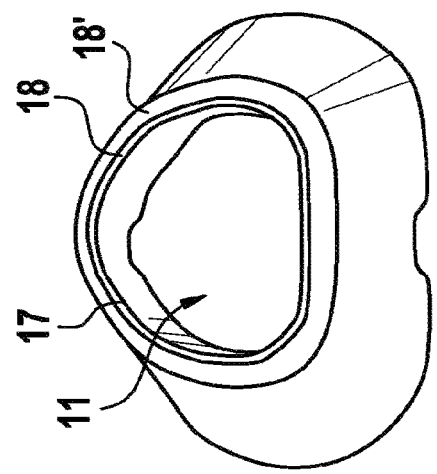
Fig. 1
a)
b)

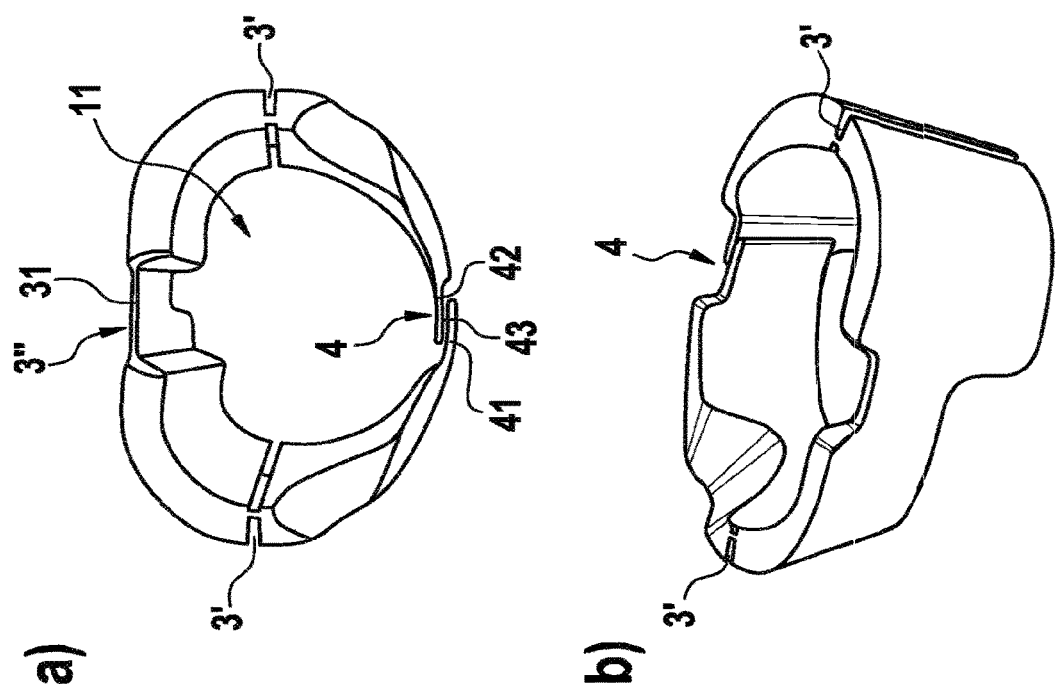
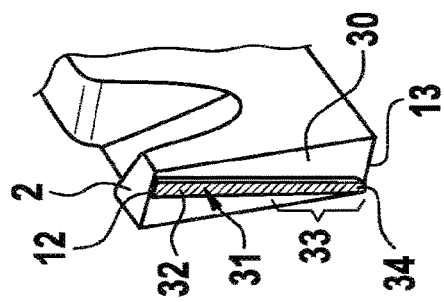
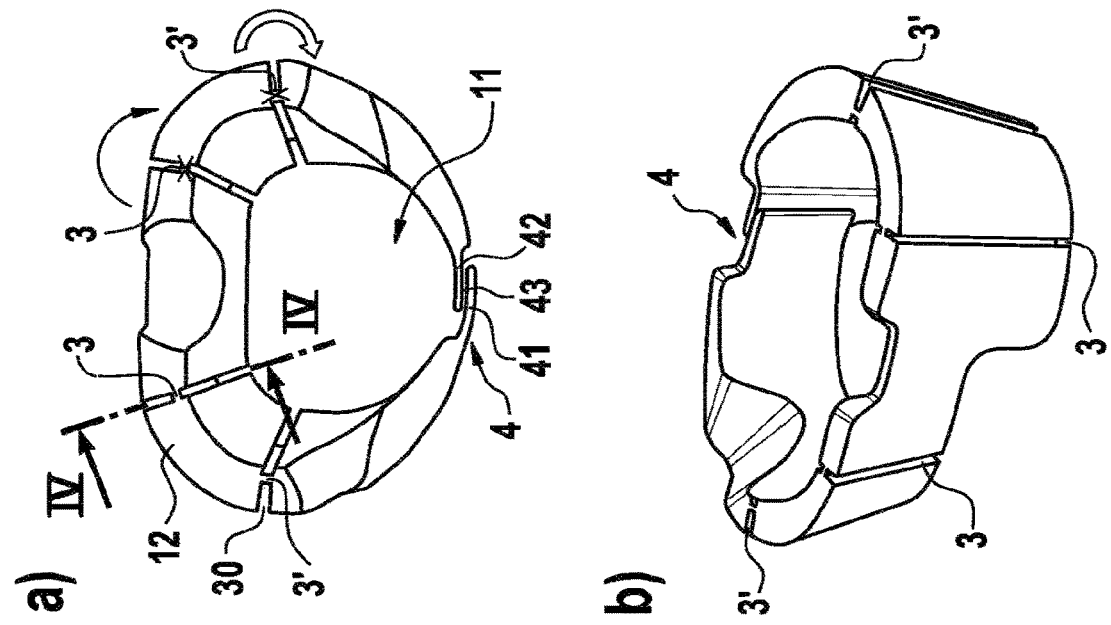

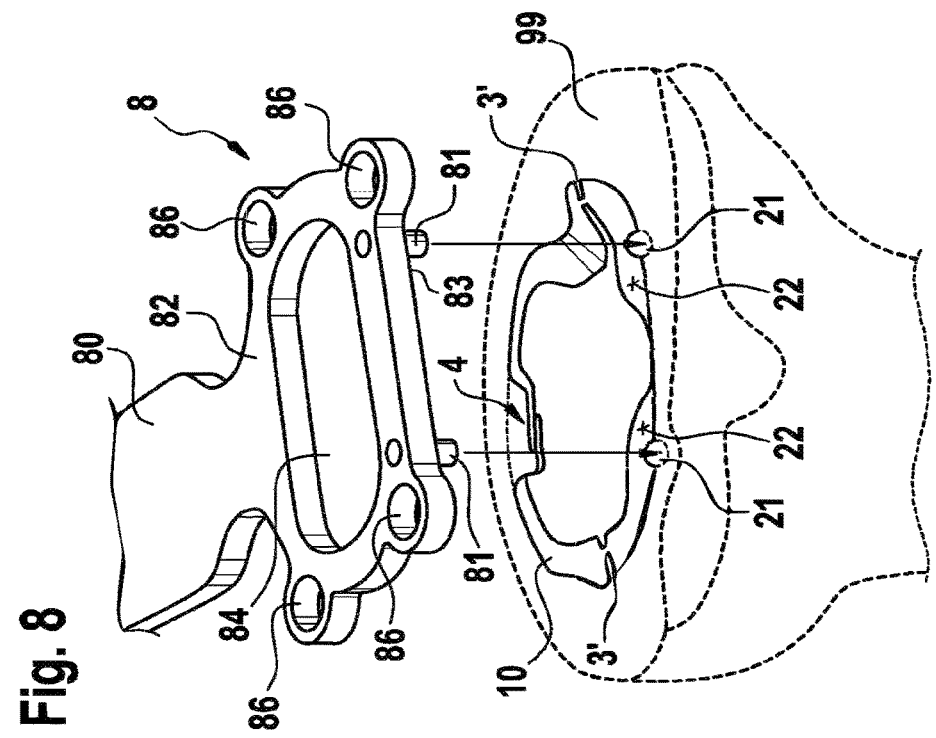
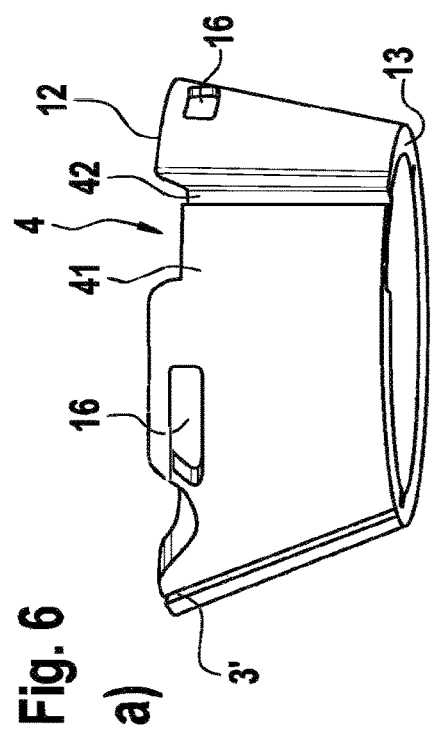
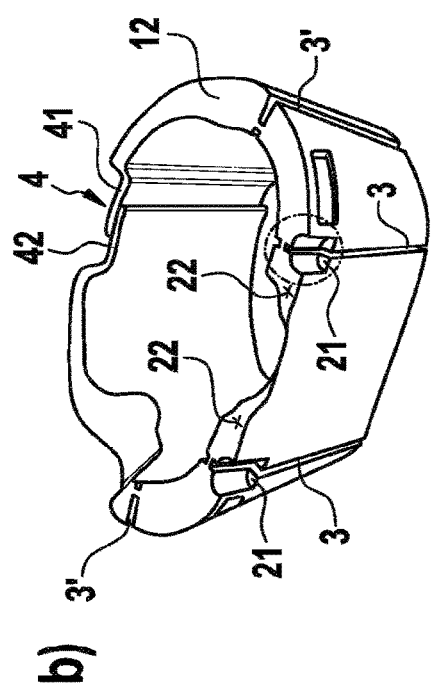
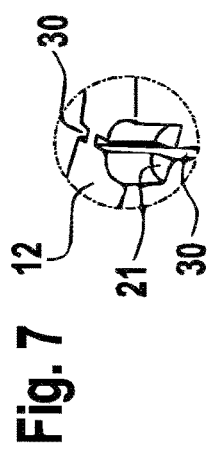

Fig. 9
a) 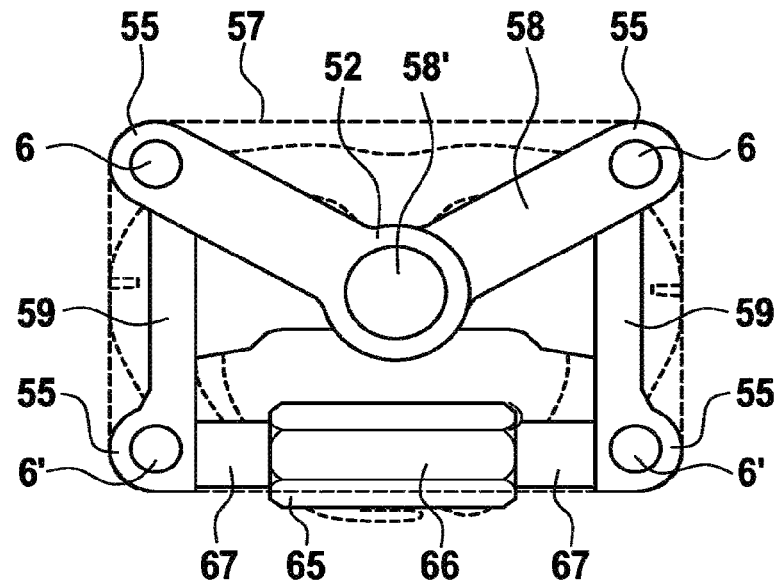
b) 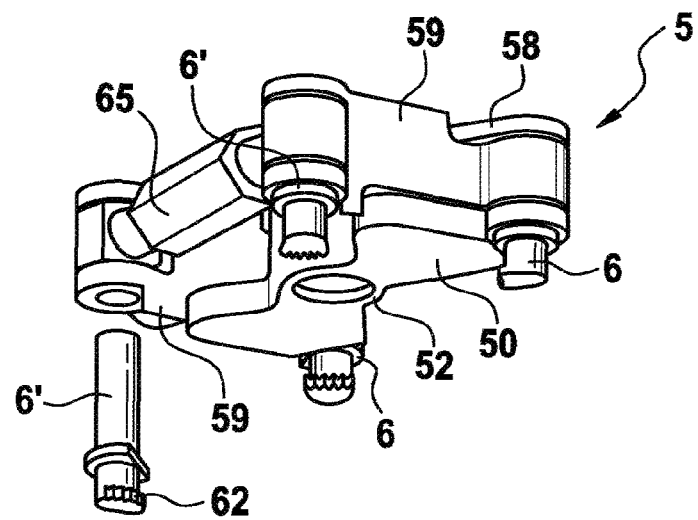

HOLLOW SLEEVE AUGMENT DEVICE AND TOOL

CROSS-REFERENCE TO RELATED APPLICATIONS

This application is a Continuation of prior-filed U.S. patent application Ser. No. 15/742,697, filed Jan. 8, 2018, which is a national stage application under 35 U.S.C. 371 of International Patent Application No. PCT/EP2016/064728, filed Jun. 24, 2016, which claims priority to European Application No. 15176128.5, filed Jul. 9, 2015, all are hereby incorporated by reference in the present disclosure in their entirety.

FIELD OF THE INVENTION

The invention relates to an augment device for a joint endoprosthesis and to a tool for this augment device, and more specifically to a tibial augment for a knee joint endoprosthesis.

BACKGROUND OF THE INVENTION

Due to diseases, injuries or wear, particularly due to high age, replacement of joints in a body, such as knee, shoulder, elbow, with endoprothetic implants is common. Due to other illness or due to an explanting of a failed endoprosthesis it is not uncommon to find an implantation site for the endoprosthesis which is pathologic, mainly due to bone defects in its vicinity. This is a problem for the surgeons since a lack of strong bone near the joint implantation side could render implantation of the endoprosthesis impossible or could lead to premature failure. Since such bone defects are encountered quite often, various approaches to remedy the situation have been devised.

In particular for such indications, wherein a joint endoprosthesis is to be used, it is known to provide an augmentation device which is configured to fill a gap left by defective bone. Such an augmentation device having the form of a hollow sleeve is e.g. disclosed in U.S. Pat. No. 8,506,645 B2. Accordingly, defective bone material will be removed and the cavity created thereby will be filled by placing of the augment device. The shape of a hollow sleeve serves a purpose of allowing the stem of a stemmed endoprosthesis to pass through its central opening, which forms a channel for the stem. The hollow sleeve itself is configured to be impacted into the cavity.

While a firm seating of the implant device is generally advantageous for long-term stability, there is a drawback in that any removal would be difficult if after some time such a need for removal were to arise. In fact, there exists a conflict of interest, firm seating of the implant device at one hand and ease of removal in case of need at the other hand.

SUMMARY OF THE INVENTION

According to some embodiments, an improved augment device and tool ease removal without compromising fixation strength.

In an augment device, in particular a tibial augment for a knee joint endoprosthesis, comprising a hollow sleeve surrounding a channel extending through the hollow sleeve from a top to a bottom of the hollow sleeve, the hollow sleeve comprising a wall having an inner face and an outer face, the hollow sleeve according to the invention comprises at least one bending joint, the bending joint being configured for compressing the channel.

By virtue of the bending joint the hollow sleeve may be compressed under a force exerted from the outside, thereby achieving a decreased circumference and width of the hollow sleeve. The effects of this is a considerable improvement in both, achieving a firm seating and facilitating removal.

Reducing the circumference enables the augment device to be put into a tight cavity of the bone more easily.

Reducing the width of the augment device means that a gap between the outer face of the augment device and surrounding bone material and bony tissue will be formed, thereby facilitating cutting of any connecting bone and tissue material which bonds the augment device to the surrounding bone. Depending on the rigidity of said bone tissue it will break under the compressive action of the augment device, thereby freeing the augment device. But even if the connecting tissue were not to break the gap formed between the outer face of the augment device and the surrounding matter facilitates insertion of a knife or a similar instrument for cutting any bonding tissue, thereby effectively freeing the augment device, too. As a result, for effecting a re-operation the augment device to be removed will be put under compressive load, thereby compressing the augment device and reducing its overall width, forming a gap to the surrounding tissue and breaking connections to the surrounding tissue. Thereby the augment device will become free and could be removed without inflicting further harm or damage to the surrounding bone. Any re-operation which may become necessary will thus be much easier since removal of the old implant device becomes much easier according to the present invention.

Since the cavity is often dimensioned to be rather tight for improved mechanical stability of the augment device and the endoprosthesis in the bone, and further to preserve as much of healthy bone as possible, there is a problem that forcing the augment device into a tight cavity may create a risk of a creating cracks in the bone. By virtue of the bending joint, the hollow sleeve could be compressed to a smaller size, thereby allowing it to be more easily placed into the cavity. Thereby a firm seating can be reached without risk for the patient.

However, there is a conflict of interests in firm seating of the augment device at one hand and creating a reliable option for removing the augment device in case of need. Such a need may arise subsequent to an implant operation, in particular if the augment device needs to be removed due to disease (e.g. inflammation) or due to wear and tear. A specific problem encountered with augment devices as opposed to regular endoprostheses is that bony material grows into the augment device, which is in principle an advantage for a solid stabilization and fixation of the augment device, however that same ingrowth of bony material contributes to complicating removal on the other hand. A similar problem arises due to usage of cement, which ensures good fixation on one hand but it is a huge liability in terms of removal. By virtue of the invention, the hollow sleeve may be compressed in situ, thereby breaking any fixation achieved by cement or ingrowth of bony material, leading to loosening and therefore facilitating removal.

As a result, the traditional contradiction of good fixation at one hand and easy of removal at the other hand could be overcome. Preferably, two or more bending joints are provided, which are further preferably arranged in a mirror symmetric fashion. This allows for a more uniform compression of the hollow sleeve. Further preferably the bending joint is configured to be elastic.

Preferably, the bending joint is formed by an integral hinge, that further preferably comprises an elongated void in the hollow sleeve and a strip of solid material spanning the void. Preferably, the strip is oriented such as to be oblique with respect to the wall, further preferably such that a lower end of the strip is positioned closer toward the outer face than an upper end of the strip which is positioned closer toward the inner face. The strip acts as a hinge providing the degree of movement required for bending a part of the hollow sleeve in respect to the other part. Further, an axis of the hinge as formed by the strip is defined by the orientation of the strip. Rather than orienting the strip to parallel to a middle chord of the wall, it is oriented oblique to it. Thereby the bending axis will not be parallel to the plane of the wall, instead it will be—in case of a generally conical shape of the augment device—parallel or at least nearly parallel to a center axis of the channel. The degree of oblique orientation is defined by the cone angle of the hollow sleeve. In other words, the oblique arrangement of the strip counteracts the effect of the conically formed wall and ensures a compressing in a horizontal plane parallel to the top cover.

In a further preferred embodiment, the strip is configured to have a reduced bending stiffness in a lower portion, preferably by means of a tapering width. Owing to the lower bending stiffness the contribution of the lower portion to the overall bending stiffness is rather small. As a result, the percentage reduction of the stiffness of a shorter bending joint is smaller than the percentage reduction of the length of that bending joint where all bending joints—although having different lengths—end at the top of the sleeve, e.g. at a hollow sleeve having a stepped bottom. This allows shortening of the augment device at its bottom without a significant effect on the bending stiffness of the bending joint in the shortened area.

Advantageously, at least one of the bending joints is arranged for enabling compression in an anterior/posterior direction. The terms "anterior" and "posterior" refer to directions of the augment device in which it is designed to be implanted to the human body. "Anterior" relates to a forward facing direction, and "posterior" to a backward facing direction. Similarly, at least one bending joint is arranged to enable compression in a lateral/medial direction. The term "lateral" refers to a direction substantial perpendicular to the anterior/posterior direction, namely to a direction away from the center away in a lateral direction, and "medial" refers to the opposite direction toward the center. Further preferably, at least two bending joints are provided, at least one enabling compression in an anterior/posterior direction and at least one enabling compression in a lateral/medial direction.

Further preferably, the hollow sleeve comprises a compensator element configured for adjusting a circumference of the sleeve in a bended state of the bending joint. The compensator element allows a degree of freedom for absorbing a reduction of the circumference which will be realized by moving the bending joints under compressive force. Preferably, the compensator element is configured as at least two overlapping tongues being in sliding relationship. Owing to the sliding relationship, the tongues maintain the bulkhead functionality even in the area of the compensator element. Further, the sliding relationship allows a variance in length and thereby the reduction of the circumference.

The wall is preferably at least partially comprised of porous material. The porous material is configured for promoting bone ingrowth, thereby achieving a much improved fixation of the sleeve to the bone.

Preferably the hollow sleeve is provided with receptacles for gripper means of a handling tool. Compressing the hollow sleeve requires considerable force, in particular if bony material that had ingrown and/or cement bonding the augment device to surrounding tissue has to be break. Exerting such force usually exceeds the capabilities of pliers or similar tools, and applying brute force with a hammer would be too risky for the patient in terms of breaking bone. For a safe and easier handling a special handling tool is provided, which features gripper means that are configured for interaction with the hollow sleeve in order to compress it. For providing a solid attachment of the gripper means, the hollow sleeve is preferably provided with receptacles. In an advantageous embodiment, the receptacles are configured as recesses for a form-fit to the gripper means. Thereby a positive engagement can be achieved. It is even further improved if the receptacles are configured with an undercut. By virtue of the undercut the handling tool can exert considerable pulling-out forces via the gripper means, without risking that the gripper means may leave there receptacles. It is to be noted that the receptacles may be a separate structure, like a recess, or may be realized by means of a porous portion into which the gripper means engages, in particular if the gripper means are preferably provided with teeth.

It is preferred that the wall is configured as a sandwich structure having a solid portion and porous portion forming the outer face, the porous portion being formed of porous material which is configured for ingrowth of bony material. By providing a porous portion on the outer face ingrowth of bony material is promoted and therefore an improved attachment and fixation of the augment device to the surrounding bone will be achieved. The same applies if cement is used as a bonding agent. Further, the porous structure may act as a receptable for being engaged by the gripper means of the handling tool.

Preferably alignment holes are provided on the top of the hollow sleeve for a proper attachment of any tools. Preferably, the alignment holes are being configured for positioning of the jig. By virtue of the alignment holes, a proper orientation of the tool, in particular the jig, can be achieved. The alignment holes provide a positive positioning of the tool, namely a jig, without requiring visual positioning. This is a considerable advantage, in particular if access to the location where the augment device is implanted should be difficult. Nevertheless, checking marks are preferably provided which are in a fixed spatial relation to the alignment holes. The checking marks are being configured such as to indicate proper positioning of the jig. A double-check can be performed to ensure that the jig is positioned properly. The checking marks can be configured for visual and/or haptic verification.

In case the wall is made of a sandwich structure the top is preferably made of solid material only and configured such that it covers essentially the complete upper side of the wall, which means the wall itself and a porous portion applied to its outer face, if such porous portion is provided. Thereby any unwanted influx of bony material or cement could be avoided. Preferably, the top and the wall form a unitary element.

According to a further embodiment of the invention, which may be the subject of independent protection, an extraction tool for an augment device as described above is provided, the extraction tool comprising a substantially flat frame having a center portion and a periphery portion, said frame defining a plane, a plurality of grippers distributedly arranged at the periphery portion, the grippers having engagement means for engaging the augment device, at least one of the grippers be movable along said plane of the frame inward towards the center portion of the frame, and a compression element actuating the at least one movable gripper. The grippers are configured such as to be enabled to attach to the augment device at its circumference, preferably by engaging the receptacles of the augment device in a form-fit manner. By actuating of the compression element the movable grippers are moved inward, thereby compressing the augment device and reducing its circumference and width. This reduction allows for an easier implanting and in particular removal of the augment device in respect to the bone where it is designed to be implanted. In particular regarding removal, a compressing of the augment device creates a gap between the circumference of the augment device and the cavity in which it is seated, thereby breaking away bony structure or cement that was fixating the augment device to the surrounding bone material. Subsequent to this breaking away, the augment device could be removed much easier. Preferably at least three grippers are provided.

Preferably at least one gripper is stationary, and the movable gripper is configured to move towards said gripper which is stationary. Thereby a gripping action could be effectively combined with an improved positive control of the positioning of the extraction tool and the augment device gripped thereby. This enables a much more precise positioning which minimizes potential damaging of surrounding tissue. Further preferably at least two movable grippers are provided, thereby achieving a wider grip with respect to the stationary gripper. The extraction tool is thus enabled to engage a bigger variation of size of augment devices while still maintaining the increased positional accuracy achieved by the stationary gripper.

The grippers may be configured for a form fit co-operating with recesses at the outer face of the augment device, or the grippers could be provided with teeth configured for piercing into the outer face of the augment device.

In a preferred embodiment, the extraction tool comprises a V-shaped stationary sub-frame with at least one movable outrigger, each outrigger carrying at least one of the movable grippers. Preferably, a plurality of outriggers are provided which are symmetrically arranged at the sub-frame. This allows for a compact configuration of the extraction tool. Further, the grippers are preferably located at corners of the frame, wherein the corners are being connected by edges of the frame. It is particularly preferred to shape the frame such that its edges are being offset to the inward with respect to an envelope line connecting the corners. Thereby free access to the outer face of the augment device from above is achieved, allowing the surgeon to freely manipulate in that area for clearing out any residual cement, bony ingrowth, or other debris surrounding the augment device. This further adds to an easier removal.

For engaging the augment device, the grippers must reach below the top of the augment device in order to engage the outer wall. In an implanted state the augment device is usually flush mounted, i.e. its side walls with their outer face are not readily accessible. In order to provide access, holes must be formed at those places where the grippers shall reach down in order to engage the outer face of the wall. For a proper positioning of these holes, a jig is preferably provided. The jig features a handle and a basic plate having guiding holes at its corners. These guiding holes serve for defining the positions at which the holes are to be drilled in order to provide access to the side wall of the augment device. The positioning of the corners with the holes at the jig is the same as the positioning of the grippers at the extraction tool, whereas the grippers are in non-actuated (idle) position.

Further preferably, a holder is provided that can be engaged to the extraction tool. The holder may preferably comprise a striking weight that could be employed to increase extraction power.

The invention further relates to a method of handling an augment device, as described above.

BRIEF DESCRIPTION OF THE DRAWINGS

In the following the invention will be described according to the accompanying drawing in an exemplary manner. In the drawings:

FIGS. 1 a, b is an overview of a first exemplary embodiment;

FIG. 2 is a schematic view showing an augment device according to the invention in situ;

FIGS. 3 a, b is a top and perspective view of a first embodiment having bending joints;

FIG. 4 is a detailed cross section through one of the bending joints;

FIGS. 5 a, b is a top and perspective view of a second embodiment having bending joints;

FIGS. 6 a, b are perspective views of a first and second embodiment showing recesses and alignment holes;

FIG. 7 shows a detailed top view of an alignment hole as shown in FIG. 6 b;

FIG. 8 shows the augment device and its alignments hole in relation to a jig in an implanted state;

FIGS. 9 a, b are top and perspective views of an extraction tool of the augments devices;

DETAILED DESCRIPTION OF THE INVENTION

Figure 10:
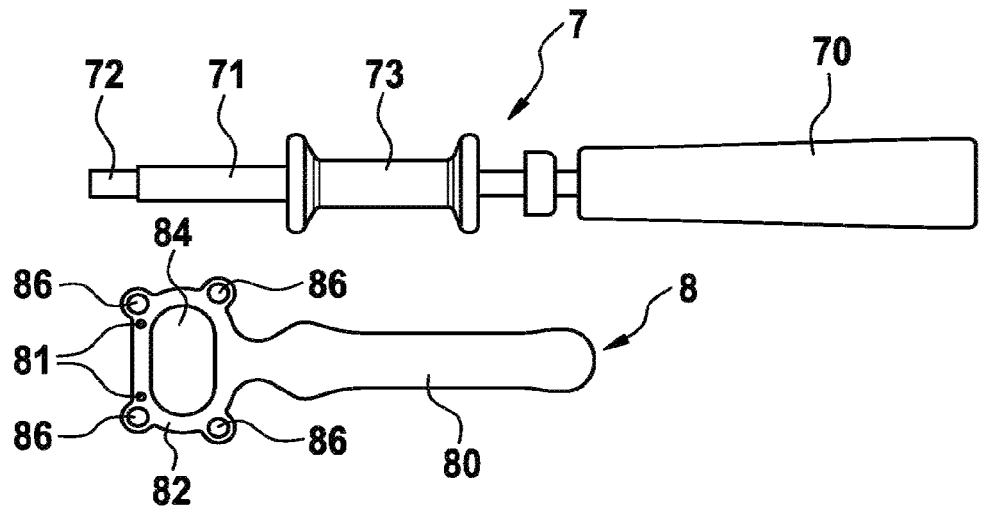
FIG. 10 shows additional instruments complementing the extraction tool.

A first embodiment of an augment device 1 according to the present invention is shown referring to FIGS. 1-4. The augment device 1 of this embodiment is preferably a tibial augment which is made of a biocompatible metallic material. It is preferably selected from a group comprising titanium alloys, pure titanium, cobalt chromium, stainless steel, tantalum and zirconium. Further preferably, the material is pure titanium (for example Ti Grade 2). This combines excellent biocompatibility with good strength and stiffness characteristics. Another preferred material is a titanium alloy (for example Ti6Al4V). This material is more regularly available, also it has a higher stiffness.

The tibial augment has a generally conic form of a hollow sleeve 10. The hollow sleeve 10 comprises a wall 17 surrounding a channel 11 which runs entirely through the augment device 1 from its top 12 to its bottom 13. The channel 11 is configured for receiving a stem of an endoprosthesis, in particular the stem 94 of a tibial part 92 of a knee prosthesis 9.

The tibial augment 1 is configured such as to be anatomically sized and shaped to fill a cavity in an upper part of a distal bone 99, namely the tibia. The augment device 1 is formed generally conically for better fitment. Its bottom side 13 is generally planar as well as its top 12.

As it can be appreciated in FIG. 2, the augment 1 is placed in the cavity of an upper portion of the bone 99, thereby forming a base on which a tibial plate 93 of the tibial component 92 of the knee prosthesis 9 is to be positioned. The knee prosthesis 9 further comprises a femur component 91 configured for rotatable interaction with the tibial portion 92. The tibial component 92 further comprises a stem 94 with ribs 94' configured to be anchored in a medullary channel of the tibia 99. The stem 94 is routed through the channel 11 of the tibial augment 1.

On the top 12 the wall 17 meets a top cover 2 which covers the complete top. The top cover 2 and the wall 17 form a unitary piece. Thereby, the wall 17 in conjunction with the top cover 2 act as a bulkhead blocking any passage of cement from the channel 11 to an external side of the hollow sleeve 10. Optionally the wall 17 features a sandwich structure having a solid portion 18 and a porous portion 18', wherein the porous portion 18' forms an outer face 15 of the hollow sleeve 10. The porous portion 18' is formed of porous material which is configured for promoting ingrowth of bony material.

The porous portion 18' is preferably made of a highly porous material having a porosity of at least 60-90%. Preferably, its pores are interconnected and elementary cells defining the pores are arranged in a regular order. The interconnected pores provide for a much improved ingrowth of bony material, and thereby ensure a good stabilization of the tibial augment 1 in the tibial bone 99.

For implantation cement may be applied for fixation of the stem 94. The cement will be applied within the channel 11 around the stem 94. In order to preserve the positive bone ingrowth effect of the porous material 17', the cement shall not reach the outer face. For this purpose the solid portion 18' of the wall 17 is provided acting as a bulkhead confining the cement to an inner portion, thereby keeping the outer face essentially cement-free. The top cover 2 ensures that no cement could spill over towards the top. A bottom cover is not necessary. However, it may be provided at the section of the bottom outward of and including the wall, thereby blocking any unwanted influx of cement into the porous material 18' on the outer face.

For a tighter fit and in particular an improved removal in case of a re-operation, the augment device 1 comprises bending joints 3, 3' (not shown in FIG. 1). Two preferred variants of the augment device having bending joints 3, 3'are shown in FIGS. 3 and 5. Both feature two sets of bending joints 3, 3' in different configurations. Generally speaking, the bending joints 3, 3' allow a bending of the hollow sleeve 10 such that it will be compressed as a whole, thereby reducing the size of the channel 11 and the outer dimension of the hollow sleeve 10. Each of the bending joints 3, 3' is formed by a void 30 in the wall 17 combined with a metal strip 31 which spans the void 30. As best appreciated in FIG. 4, the metal strip 31 is of solid material and runs from the top 12 to the bottom 13 of the hollow sleeve 10. The metal strip 31 is configured such as to provide the bending joint 3, 3' with elasticity in respect to a bending movement. By varying the dimensions of the metal strip 31 or by choosing a different material the characteristics can be adjusted. As shown in more detail in FIG. 4, the strip 31 is oriented oblique with respect to the wall 17 such that a lower end 34 of the strip 31 is positioned close toward the outer face 15 of the wall 17 and the upper end 32 of the strip 31 is placed close to the inner face of the wall 17. By virtue of this arrangement, the strip 31 is oriented essentially parallel to a center axis of the channel 11. Thickness of the strip 31 at a lower portion 34 is reduced. To this end, the strip 31 is configured such as to have a tapering width towards its lower end 34. By virtue of this tapering, the most bending force will be created by the upper part of the strip 31, whereas the lower portion 34 will only contribute to the bending force to a much lesser degree.

The bending force and movement effected thereby is depicted in FIG. 3a. Two pairs of bending joint 3, 3' are provided in a mirror symmetric configuration. A first set of bending joints 3 is placed at a rear wall of the hollow sleeve 10. By exerting a bending force, the bending joints 3 allow for a movement in a rotational direction as indicated by the single arrow. Thereby an axis of bending defined by the bending joints 3 provides for an elasticity in a medio/lateral (ML) direction.

A second set 3' is provided which is arranged in a mirror symmetric configuration at the side portion of the hollow sleeve 10. The bending joints 3' provide a range of motion as depicted by the double arrow. This provides for an axis of bending which gives anterior/posterior (AP) elasticity. As a result, by providing both pairs of bending joints 3, 3' elastic compressibility in two dimensions is achieved, namely one in ML direction and another in AP direction. The center of rotation for the bending joints providing elastic compressibility in ML direction is shown with a symbol resembling a letter "X" whereas the elastic compressibility in AP direction is shown by symbol resembling a cross in a circle, each showing the effective center of rotation.

In the variant as shown in FIG. 5 a, b the second set 3' for providing elastic compressibility in AP direction (anterior/posterior) is identical to that of the first variant depicted in FIG. 3 a, b. However, the first set of bending joints providing a range of motion in medio-lateral (ML) direction is configured differently, namely as a concentrated element in which the two bending joints 3 of FIG. 3a are combined to one bending joint 3" which has a wider dimension. The functionality is essentially identical to FIG. 3 a, b, namely the bending joint 3" provides elastic compressibility in ML direction.

By exerting bending force the width of the inner channel 11 will be reduced. Thereby, its circumference will be reduced. In order to enable the hollow sleeve 10 for such a reduction, a compensator element 4 is provided. In the depicted embodiments it is arranged at an opposite, front side of the hollow sleeve 10 to the bending joints 3. The compensator element is comprised of two tongues 41, 42 arranged at a left and a right portion of the hollow sleeve 10. The tongues 41, 42 are arranged in an overlapping configuration, leaving just a tiny gap 43 therebetween. The tongues 41, 42 slide along each other under the effect of a bending motion with the bending joints 3, 3', thereby promoting compressibility. The gap 43 is dimensioned such as to be small enough to block leakage of cement.

As best shown in FIG. 6 a, b a set of receptacles 16 are provided in the vicinity of the top 12 of the wall 17. The receptacles 16, two of which are placed on a front side of the augment device 1 at a left and right portion and further two are placed on a back side of the augment device 1 also at a left and a right portion. The front and the back side are shown in FIG. 6 a, b respectively. Receptacles 16 are configured as recesses which are enabled to provide a form-fit with grippers of an extraction tool 5, as will be explained in detail further below. Further, alignment holes 21 are provided in the top cover 2 of the augment device 1. The alignment holes 21 are configured as blind holes which are laterally open to the outer face 15. The alignment holes 21 are configured for accepting alignment pins 81 of a jig 8. For refined positioning the alignment holes 21 are preferably slightly conical in shape, as it is shown in more detail in FIG. 7. Further, checking marks 22 could optionally be provided at a top 12 of the augment device 1. The checking marks 22 are set in a fixed spatial relation to the alignment holes 21. The checking marks 22 are configured such as to indicate proper positioning of the jig 8 in respect to the augment device 1. This act as a further means of checking whether the jig 8 is positioned correctly in respect to the augment device 1, thereby acting as a verifying means in addition to the alignments holes 21.

The relation between the jig 8 and the augment device 1 in its implanted state in a tibia 99 is shown in FIG. 8. The tibia 99 is shown with dashed lines. At its proximal end, the augments device 1 is positioned in a cavity. A top 12 of the augment device 1 is substantially flush with the upper surface of the tibia 99. The jig 8 is provided with two alignment pins 81 projecting downwards from a lower side 83, the alignment pins 81 being spaced such far apart as the spacing of the two alignment holes 21 of the augment device 1 are spaced, and they are configured to being engaged in said alignment holes 21, thereby providing a positive positioning of the jig 8 in respect to the augment device 1. Proper positioning of the jig 8 in respect to the augment device is important since the jig 8 is further provided with a plurality of guiding holes 86 which are positioned at each corner of the jig 8. The guiding holes 86 indicate those positions, at which holes are to be bored in order to provide sufficient space for incursion of grippers 6 of an extraction tool 5. The jig 8 is generally of a flat plate like structure having a planar upper side 82 and a substantially planar lower side 83. The four guiding holes 86 are arranged at the four corners. In the middle a large central opening 84 is provided in order to allow full access to the inner channel 11 of the augment device 1. For manipulating of the jig 8 a handle 80 is provided which is formed as a unitary piece at a longer edge of the jig 8. On the opposite side the alignment pins 81 are mounted such that they are projecting from the lower side 83 of the jig 8. Placing of the jig 8 onto the augment device 1 is illustrated by two arrows in FIG. 8, the arrows showing the alignment pins 81 and their trajectory into the alignment holes 21.

The extraction tool 5 for extracting the augment device 1 of the tibia 99 is depicted in FIG. 9 a, b. It comprises a substantially flat frame 50 having a center portion 52 and a periphery portion. The substantially flat frame 50 comprises a V-shaped stationary sub-frame 58 in the center portion 52 and two movable outriggers 59 at a left and right periphery portion. Each movable outriggers 59 is affixed by means of a swivel joint to the respective outer end of the V-shaped stationary sub-frame 58. The other ends of the outriggers 59 are connected with each other by a compression element 65. The compression element 65 is configured to be compressible upon actuation by an actuating tool (not shown); in the depicted embodiment the compression element 65 is a double threaded nut 66 riding along counter-threads of stubs 67 mounted at the free ends of the outriggers 59, thereby moving the two free ends of the outriggers 59 toward each other in a planar fashion. At either end of both outriggers 59 one gripper 6 is mounted, each gripper having teeth for engaging the augment device 1. The grippers arranged in the stationary sub-frame 58 are denominated by reference number 6, while those grippers arranged at the movable elements, namely the outriggers 59 are denominated with a reference number 6'. The grippers 6, 6' are located at the four corners of the substantial flat frame 50 and the movable grippers 6' move in a plane defined by said frame 50.

It is important to note that the edges of the frame 50, including its stationary sub-frame and the outriggers 59, are not coincident with an imaginary envelope line 57 connecting the four corners 55; rather, the edges of the frame 50 with the sub-frame 58 and the outriggers 59 are being offset that, namely set-off towards the center portion 52. By virtue of this, access to the outer face 15 of the wall 17 of the augment device 1 to which the extraction tool 5 is to be attached is much facilitated, since owing to the off-set configuration of its edges the frame 50 does not block access. This is depicted in FIG. 9a, wherein the outline of the augment device 1 is shown by a dashed line.

The grippers 6, 6' are provided with of engagement means for engaging the augment device 1. One embodiment is to have teeth 62 at the lower end of the gripper 6, 6' which are configured for engaging into the receptacles 16 of the augment device 1. In case no receptacles are provided, then teeth 62 at the grippers 6, 6' serve the purpose of piercing into the outer face 15 of the augment device, thereby engaging it and affixing the extraction tool 5 to the augment device 1. An alternative embodiment would be to have just projections without toothing, which would sufficient for engaging the receptable 16. Preferably, the grippers 6, 6' are held at the corners 55 in such a manner that they are easily replaceable (s. FIG. 9b).

In the stationary sub-frame 58 a central opening 58' is provided which is configured for being engaged by a holder 7. The holder 7 comprises a shaft 71 having a handle 70 at its rear end. At its front end the holder 7 features a threaded tip 72 which can be brought into engagement with a complementary thread at the center hole 58'. Optionally, a striking weight 73 is slidably mounted at the shaft 71, for an amplified pull-out force. The holder 7 is shown in FIG. 10 together with the jig 8, forming an instrument set in conjunction with the extraction tool 5 (FIG. 9 a, b).

Figure 11:
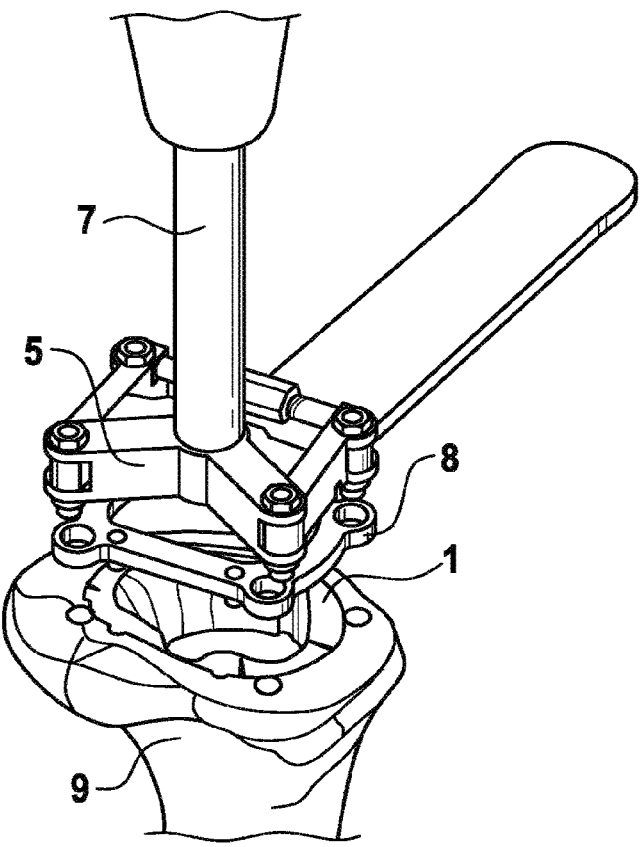
FIG. 11 shows a mutual relationship between the augment device, jig and extraction tool.

The relation of the jig 8 to the extraction tool 5 and its holder 7 is shown in FIG. 11. The jig 8 is to be placed between the augment device 1 on its top, and on the top of the jig 8 the extraction tool 5 is shown.

Figure 12:
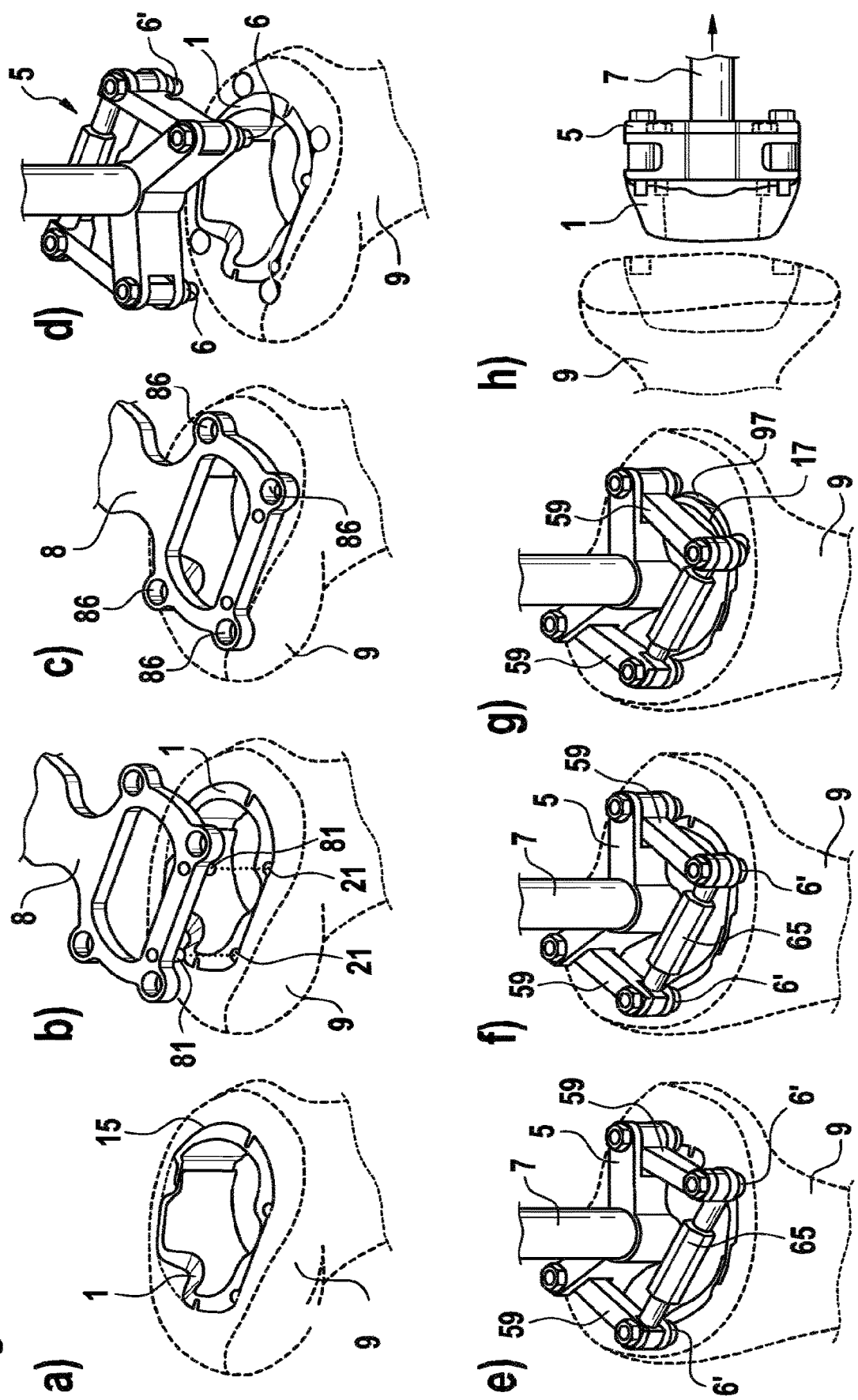
FIGS. 12 a-h show steps of operation.

The method of operation for an inventive use of the instrument set and the augment device accord to the present invention is shown stepwise in FIG. 12 a-h. In FIG. 12a a tibia 99 having an augment device 1 which is to replaced is shown. It is assumed that the augment device 1 is connected quite strongly to the tibia 99, in particular by bony ingrowth into a porous structure 18' on the outer face 15 of the wall 17. Due to that ingrowth removal of the augment device 1 is difficult. In a first step shown in FIG. 12b, the jig 8 is to be brought into position overhead of the augment device 1. It is positioned such that its alignment pins 81 on the lower surface of the jig 8 are in line with the alignment holes 21 of the augment device 1 (see dotted lines in FIG. 12b). FIG. 12c shows the jig 8 brought into position in an aligned relationship, wherein the alignment pins 81 are centered in the alignment holes 21. The jig 8 is now sitting flat on the top of the augment device 1. Its guiding holes 86 at its four corners define holes that are to be drilled in order to make room for inserting the grippers 6, 6' at a later stage. Once these holes are drilled, the jig 8 may be removed. The drilled holes after removal of the jig 8 are shown in FIG. 12d. Then the extraction tool 5 is placed overhead of the augment device 1 and positioned such that its grippers 6,6' are aligned with the four holes created by drilling through the guiding holes 86 (s. FIG. 12d). The extraction tool 5 can then be lowered into position on top of the augment device 1, and the grippers 6, 6' with their engagement means (teeth 62) will enter into the said drilled holes (s. FIG. 12e, please note that FIG. 12 *e-h* depict a view from the opposite side). The teeth 62 are now so far lowered as to be approximately at the height at which the receptacles 16 are placed at the augment device 1. In a next step the compression element 65 is actuated by a tool (not shown), and the movable grippers 6' mounted on the outriggers 59 are brought into an inward position (s FIG. 12*f*). As a result, the extraction tool 5 is securely affixed to the augment device 1 by virtue of the engagement means (teeth 62) of the grippers 6, 6' being engaged in the receptacles 16. In principle the augment device 1 could now be removed by pulling on the extraction tool 5. However, due to the bony ingrowth the augment device 1 is likely to be held in position. In order to break the augment device free, the compression element 65 is actuated further by the tool (not shown), namely so far that the bending joints 3 are moved and the wall 17 of the augment device 1 is compressed. Thereby the outer circumference of the wall 17 is decreased, producing a gap 97 between the original cavity in which the augment device 1 was placed and the actual outer circumference of compressed augment device. Due to this gap 97 any connection due to bony ingrowth between surrounding bony tissue and the porous outer face 15 of the augment device 1 will break away. Thereby the augment device 1 becomes free. Subsequently, it can be pulled out straight by the extraction tool 5, as shown in FIG. 12*h*.

What is claimed:

1. An augment device for a joint endoprosthesis comprising:
    a hollow sleeve surrounding a channel extending through the hollow sleeve from a top to a bottom of the hollow sleeve, the hollow sleeve comprising a wall having an inner face, an outer face, and
    at least one bending joint configured for compression of the channel,
    wherein the at least one bending joint is formed by an integral hinge that comprises an elongated void in the hollow sleeve and a strip of solid material spanning the void,
    wherein the strip is oriented such that a lower end of the strip is positioned closer to the outer face than an upper end of the strip, and wherein the upper end of the strip is positioned closer toward the inner face than the lower end of the strip.

2. The augment device of claim 1, wherein the strip is oriented such as to be oblique with respect to the wall.

3. The augment device of claim 1, wherein the strip comprises a tapering width towards the lower end, in which the width at a lower portion of the strip is less than the width at an upper portion.

4. The augment device of claim 3, wherein the at least one bending joint is configured to have a lower bending stiffness in the lower portion as compared to the upper portion.

5. The augment device of claim 1, wherein the at least one bending joint is arranged as to enable compression in a lateral-medial direction.

6. The augment device of claim 1, wherein the at least one bending joint is arranged to enable compression in an anterior-posterior direction.

7. The augment device of claim 1, wherein the hollow sleeve comprises a compensator element configured for adjusting a circumference of the hallow sleeve in a bended state of the at least one bending joint.

8. The augment device of claim 7, wherein the compensator element is configured as two overlapping tongues arranged in a sliding relationship.

9. The augment device of claim 1, wherein the hollow sleeve comprises receptacles for receiving a handling tool.

10. The augment device of claim 9, wherein the receptacles are configured as recesses that may form-fit with grippers.

11. The augment device of claim 10, wherein the receptacles include an undercut.

12. The augment device of claim 1, wherein the top of the hollow sleeve includes alignment holes that are configured for positioning a jig.

13. The augment device of claim 12, further comprising checking marks located in a fixed spatial relation to the alignment holes, the checking marks being configured to indicate proper positioning of the jig.

14. The augment device of claim 1, wherein the wall is a sandwich structure having a solid portion and a porous portion, the porous portion forming the outer face and being formed of porous material which is configured for ingrowth of bony material.

15. The augment device of claim 1, further comprising a top cover made of solid material and configured to cover the top of the hollow sleeve.

16. The augment device of claim 15, wherein the top cover and the wall form a unitary element.

17. The augment device of claim 1, wherein the wall is at least partially comprised of porous material configured for promoting bone ingrowth.

18. The augment device of claim 1, wherein the augment device is a tibial augment for a knee joint endoprosthesis.

19. The augment device of claim 1, wherein the at least one bending joint is two bending joints, and wherein the two bending joints are arranged in mirror symmetry.

* * * * *